(12) United States Patent
Minoguchi et al.

(10) Patent No.: US 7,338,462 B2
(45) Date of Patent: Mar. 4, 2008

(54) TAMPON APPLICATOR HAVING A FORCE CONTROLLER

(75) Inventors: Ryo Minoguchi, Blue Ash, OH (US); Diana Lynne Gann, Lebanon, OH (US); Thomas Ward Osborn, III, Clifton, OH (US); James Douglas Still, Cleves, OH (US); Letha Margory Hines, Cincinnati, OH (US); Ricky Alan Pollard, Moscow, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/109,375

(22) Filed: Apr. 19, 2005

(65) Prior Publication Data

US 2005/0277866 A1    Dec. 15, 2005

Related U.S. Application Data

(63) Continuation-in-part of application No. 10/792,351, filed on Mar. 3, 2004.

(51) Int. Cl.
*A61F 13/20* (2006.01)
(52) U.S. Cl. .......................................... 604/14; 604/15
(58) Field of Classification Search ............. 604/11–18
See application file for complete search history.

(56) References Cited

U.S. PATENT DOCUMENTS 1,969,671 A    8/1934  Nelson
2,351,836 A  *  6/1944  Popper ..................... 604/16
3,397,695 A    8/1968  Voss
3,674,025 A    7/1972  Bleuer
3,706,311 A   12/1972  Kokx (Continued)

FOREIGN PATENT DOCUMENTS

GB          500 742 A        2/1939
WO     WO 00/78260 A1  * 12/2000

OTHER PUBLICATIONS

PCT International Search Report dated Jun. 21, 2005.
PCT International Search Report dated Sep. 15, 2006.

*Primary Examiner*—Tatyana Zalukaeva
*Assistant Examiner*—Michael G Bogart
(74) *Attorney, Agent, or Firm*—James E. Oehlenschlager; Ingrid N. Hackett; David M. Weirich

(57) ABSTRACT

A tampon and a tampon applicator in combination for expulsion of a tampon. The tampon applicator has a tampon holder tube. The tampon holder tube has a hollow interior portion, a first end dimensioned for insertion into a vaginal cavity, a second end positioned oppositely to the first end, a force controller, and at least one side expulsion member. The side expulsion member has a weakened region located at its base. The tampon has a body having a first end, center, and a second end; body has a joined portion; the body has a plurality of absorbent strips joined at the joined portion. The strips are selected from the group consisting of nonwoven materials, films, woven materials, absorbent foams, superabsorbent polymers, and mixtures thereof. The tampon is housed within the hollow interior portion of the tampon holder tube in a pre-expelled position.

16 Claims, 13 Drawing Sheets

U.S. PATENT DOCUMENTS

| | | |
|---|---|---|
| 3,760,808 A | 9/1973 | Bleuer |
| 3,981,305 A | 9/1976 | Ring et al. |
| 4,312,348 A | 1/1982 | Friese |
| 4,479,791 A | 10/1984 | Sprague |
| 4,592,740 A | 6/1986 | Mahruki |
| 5,279,541 A | 1/1994 | Frayman et al. |
| 5,348,534 A | 9/1994 | Tomaszewski et al. |
| 5,531,674 A | 7/1996 | Frayman et al. |
| 5,569,177 A | 10/1996 | Fox |
| 5,693,009 A | 12/1997 | Fox |
| 5,766,145 A | 6/1998 | Fox |
| 5,817,047 A | 10/1998 | Osborn |
| 5,928,183 A | 7/1999 | Fox |
| 6,019,744 A | 2/2000 | Altdorf et al. |
| 6,024,716 A | 2/2000 | Rejai |
| 6,056,714 A | 5/2000 | McNelis |
| 6,095,998 A | 8/2000 | Osborn |
| 6,254,566 B1 | 7/2001 | Buck et al. |
| 6,270,470 B1 | 8/2001 | Buck et al. |
| 6,302,862 B1 | 10/2001 | Osborn |
| 6,358,223 B1 | 3/2002 | Mackay et al. |
| 6,450,985 B1 | 9/2002 | Schoelling et al. |
| 2003/0236499 A1 | 12/2003 | Fedyk |
| 2005/0197615 A1 | 9/2005 | Gann et al. |
| 2005/0256482 A1 | 11/2005 | Minoguchi et al. |
| 2005/0273044 A1 | 12/2005 | Gann et al. |
| 2005/0277866 A1 | 12/2005 | Minoguchi et al. |
| 2005/0277867 A1 | 12/2005 | Minoguchi et al. |

\* cited by examiner

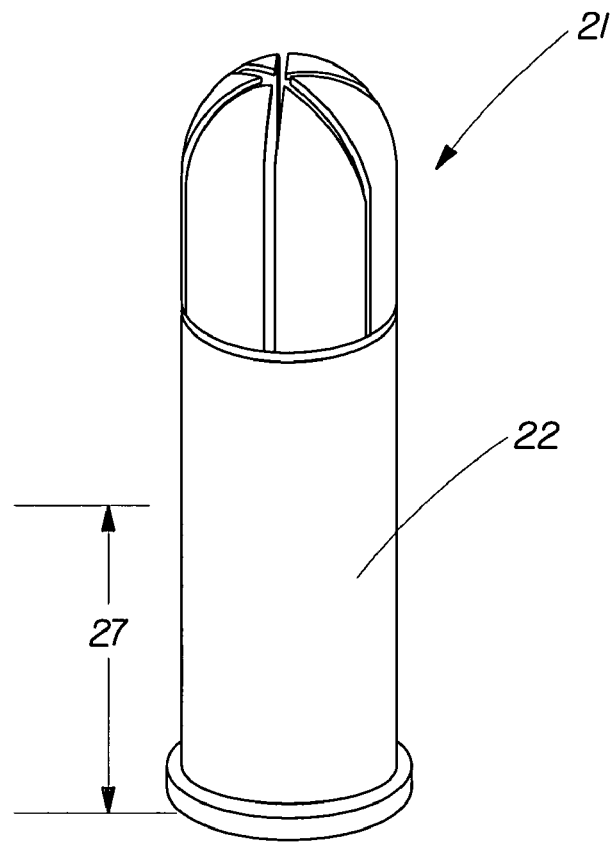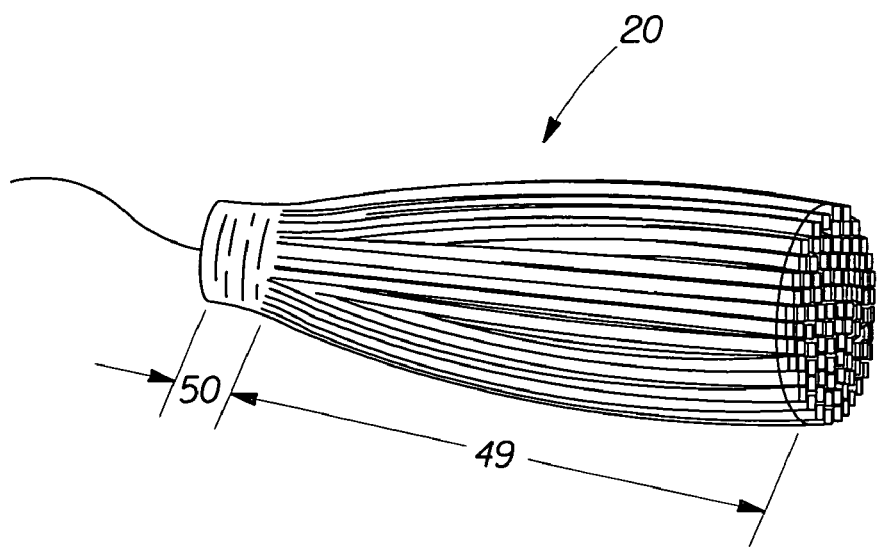
Fig. 4

TAMPON APPLICATOR HAVING A FORCE CONTROLLER

CROSS REFERENCE TO RELATED APPLICATIONS

This application is a continuation-in-part of U.S. application Ser. No. 10/792,351, filed Mar. 3, 2004, pending.

FIELD OF THE INVENTION

The present invention relates to a novel tampon applicator having an expulsion force controller providing expulsion of a tampon.

BACKGROUND OF THE INVENTION

It is known that the internal vaginal cavity in its normal state has a shape of a flattened bag with its minimum width near the introitus and its maximum width near the cervix. It is desirable, therefore, when considering a tampon for catamenial use, to provide a structure which, in its initial state, is of a size small enough to pass through the vaginal orifice without discomfort, and once delivered and placed inside the vaginal cavity beyond the restrictions of the orifice, can increase its dimension, particularly in the lateral direction, to cover substantially large portions of the vaginal surface from one side to the other to prevent early bypass of the menstrual discharges from the cervix. This side-to-side coverage is a preferred object of this invention. Further, since the vaginal wall in its normal state is flaccid and has multiple folds and wrinkles which provide channels through which a significant portion of the menstrual fluids normally flow, it is also important that the absorbent tampon be as soft and conformable as possible to conform to the shape of the vaginal cavity and fit within these channels to minimize leakage.

Generally, absorbent catamenial tampons are small, highly compressed, cylindrical rigid plugs about 5 to about 20 mm in diameter and from about 35 to about 60 mm in length. Because of the need for absorbent capacity, they are usually formed from batts much larger in size than the vaginal orifice and compressed to the small size indicated above to facilitate insertion. As fluid is absorbed, these compressed tampons are designed to re-expand. While it has been found that these compressed tampons perform their intended function tolerably well, even the best of them do not re-expand sufficiently, or fast enough, to provide good transverse coverage against leakage even though the vertical blockage may be satisfactory. Further, most of these tampons often use only a small portion of their absorptive capacity before leakage. Since these tampons rely on some fluid absorption to re-expand, it is clear that fluid bypass and leakage can occur prematurely, particularly, immediately or soon after the time of insertion.

Fortunately, it has been found during development of the present invention that a tampon, in particular, a deformable tampon, inserted using the tampon applicator constructed according to the invention discussed herein yields the side-to-side coverage of the vaginal cavity immediately or soon after the time of insertion, even with no help of fluid absorption, and thereby can provide even further improvements in leakage protection, comfort, and low wearing awareness, as compared to currently marketed tampon applicators and previous attempts to improve tampon applicators.

SUMMARY OF THE INVENTION

This invention relates to a tampon and a tampon applicator in combination for expulsion of a tampon. The tampon applicator has a tampon holder tube. The tampon holder tube has a hollow interior portion, an interior surface, an exterior surface, a longitudinal axis, an outer perimeter. Moreover, the tampon holder has a first end dimensioned for insertion into a vaginal cavity, a second end positioned oppositely to the first end, a force controller, and at least one side expulsion member positioned at the first end of the tampon holder tube. The side expulsion member has a weakened region located at its base. The tampon has a body having a first end, a center, and a second end. The body has a joined portion. The body has a plurality of absorbent strips joined at the joined portion. The strips are selected from the group consisting of nonwoven materials, films, woven materials, absorbent foams, superabsorbent polymers, and mixtures thereof. The tampon is housed within the hollow interior portion of the tampon holder tube in a pre-expelled position.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 1a is a perspective view of a tampon applicator and tampon in its pre-expelled state.

FIG. 1b is a top view of the tampon applicator of FIG. 1a.

FIG. 4 is a perspective view of the tampon before insertion into the tampon applicator.

DETAILED DESCRIPTION OF THE INVENTION

The following are terms which will assist the reader in best understanding the features of the invention and not to introduce limitations in the terms inconsistent with the context in which they are used in this specification. These definitions are not intended to be limiting.

Figure 5:
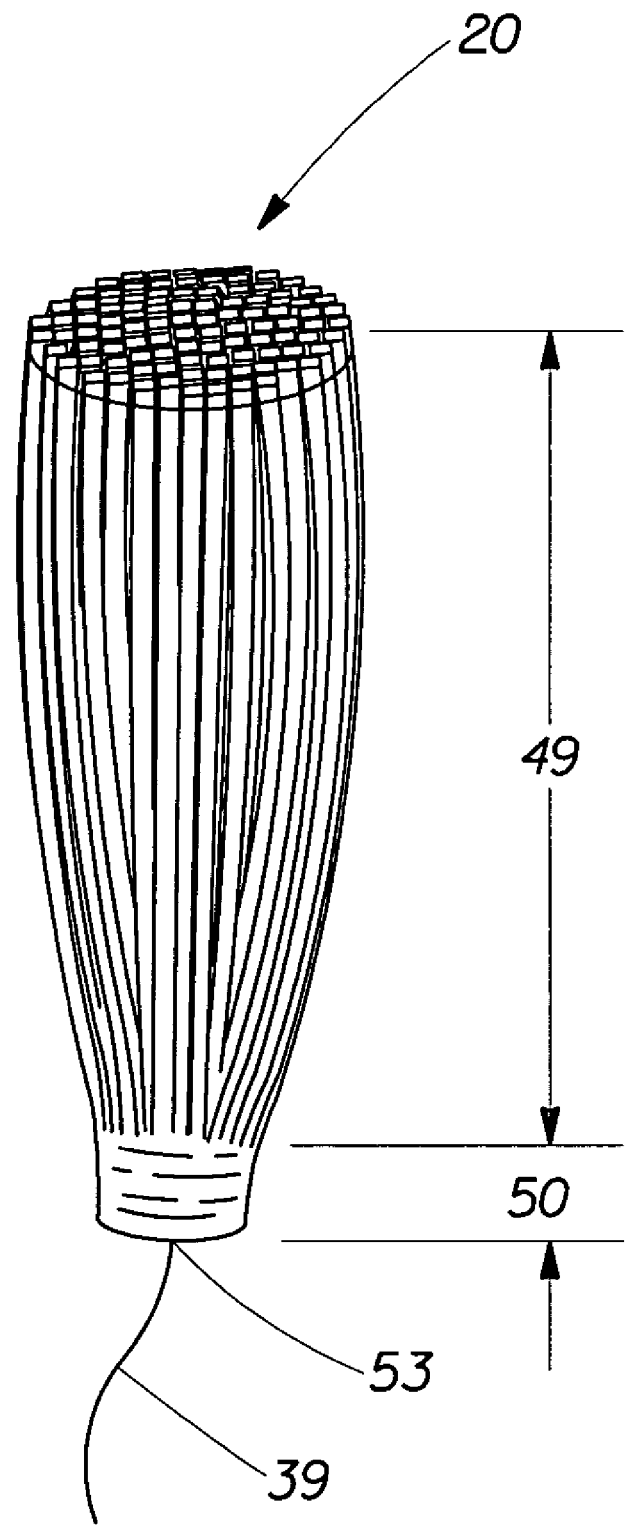
FIG. 5 is a perspective view of the tampon.

As used herein, the term "tampon," refers to any type of absorbent structure that is inserted into the vaginal canal or other body cavities for the absorption of fluid therefrom, to aid in wound healing, or for the delivery of active materials, such as medicaments, or moisture. In one non-limiting example, the term "tampon" can be as meant and as seen in FIG. 5. As seen in FIG. 5, the tampon 20 has a first portion 49 and a second portion 50. The second portion 50 has a trailing edge 53 such as that disclosed in currently pending and commonly assigned, U.S. patent application Ser. No. 10/836,892, filed Apr. 30, 2004, entitled "Tampon Comprising a Plurality of Strips or Cords," to Minoguchi, et al, Case 9615.

Figure 1:
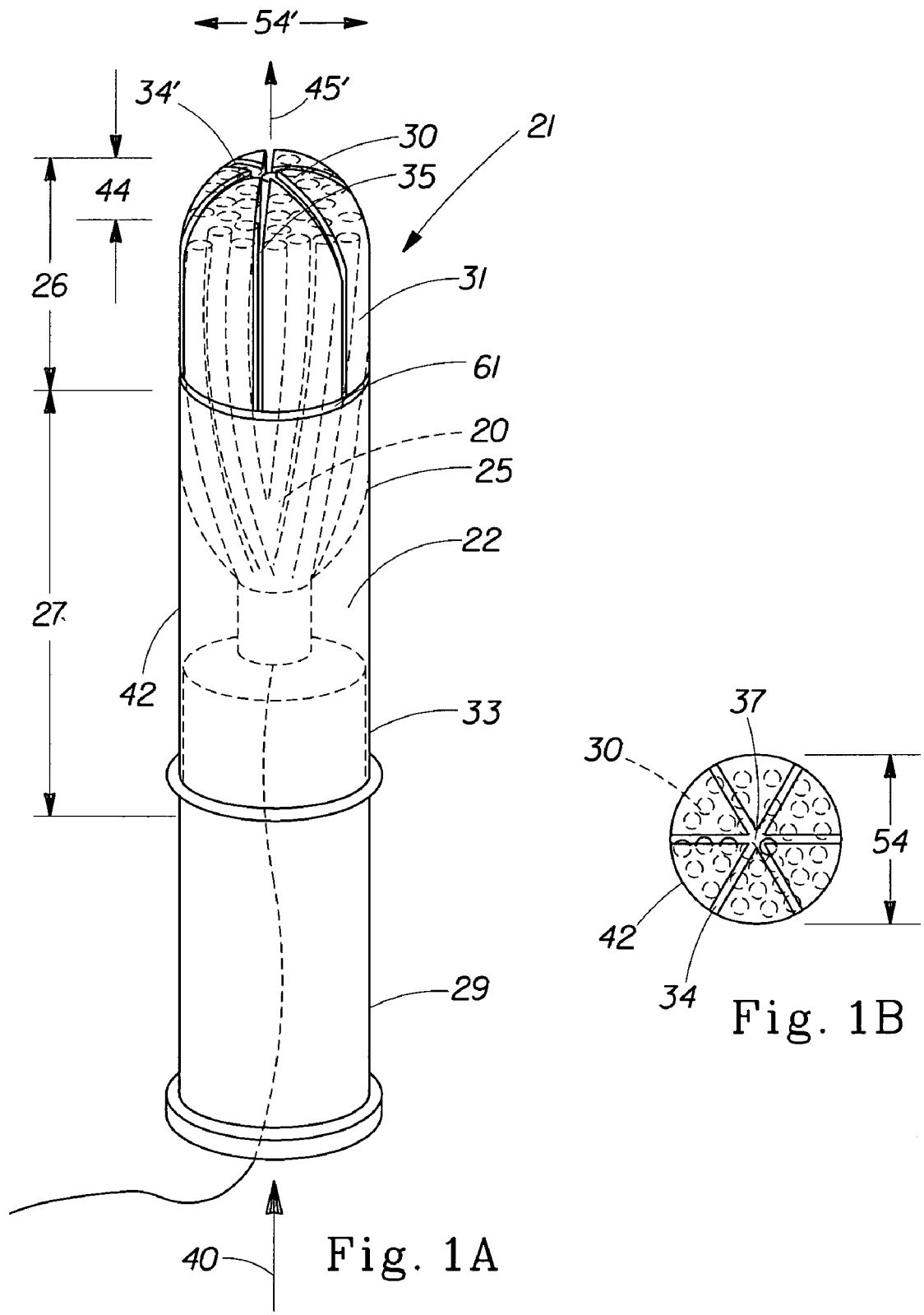

By the terms "ready position" or "pre-expelled position," it is meant herein and as seen in FIG. 1a, a position in which the tampon 20 is placed or packed into the tampon holder tube 22 and positioned for the tampon's 20 successful expulsion through the tampon holder tube 22.

By the terms "directionally expel," "directed expulsion," or "directional expulsion," it is meant herein and as seen in FIG. 1a, that embodiments of the tampon applicators 21 of the present invention will expel a tampon 20 along the longitudinal axis 45 and cause it to be placed in a position within the vaginal cavity to expand outwardly towards the walls of a female user's vaginal cavity. Such directional expulsion causes the tampon applicator 21, when inserted into the vaginal cavity of a female user, to allow the tampon 20 to expand in the transverse direction thus providing improved coverage of a female user's vaginal cavity.

Figure 3A:
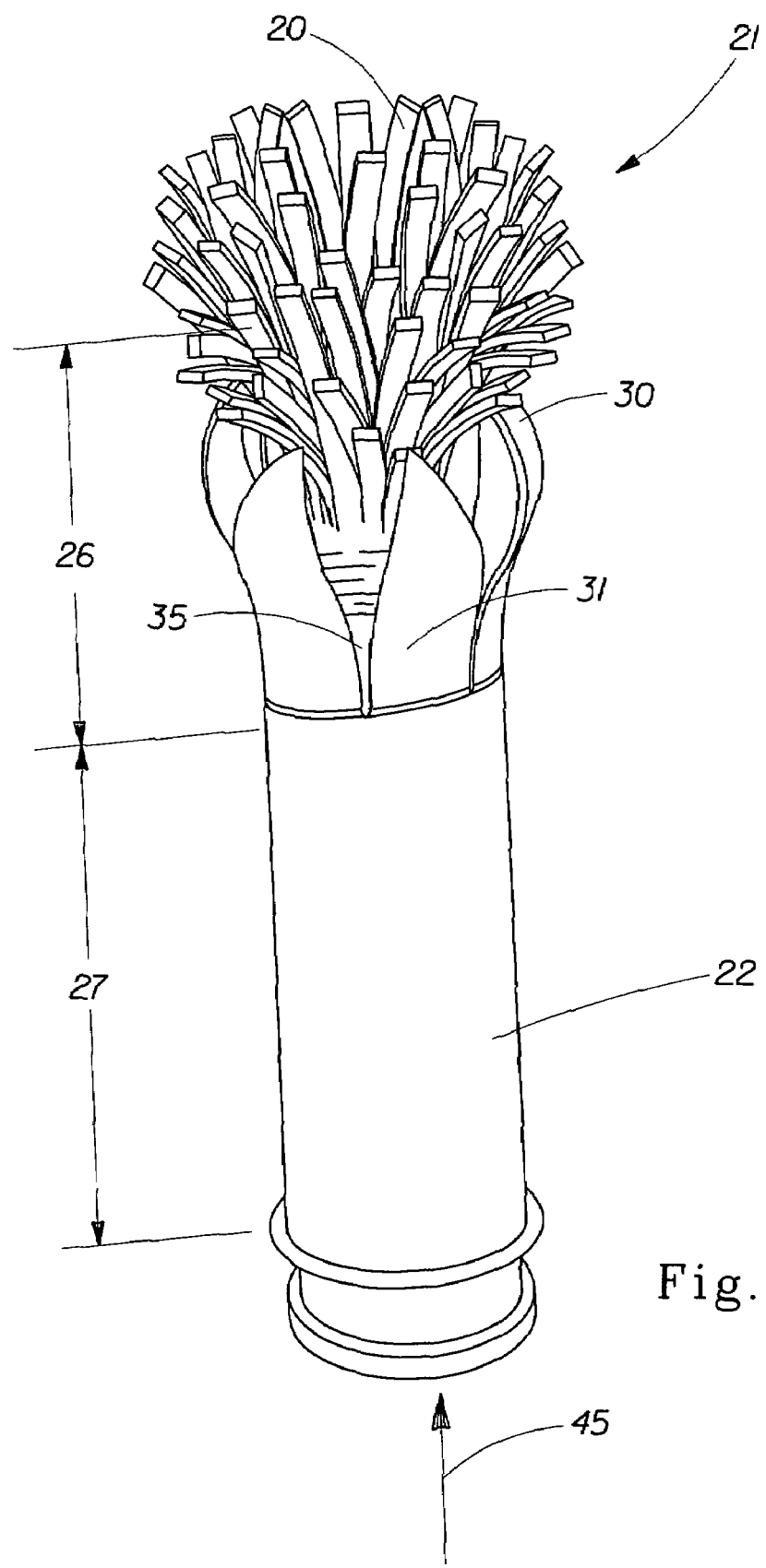
FIG. 3a is a perspective view of a tampon applicator and the tampon in its expelled state.

The term "expelled," as used herein and as seen in FIG. 3a, is meant the position after the tampon 20 is forced out of the tampon applicator 21.

Figure 3B:
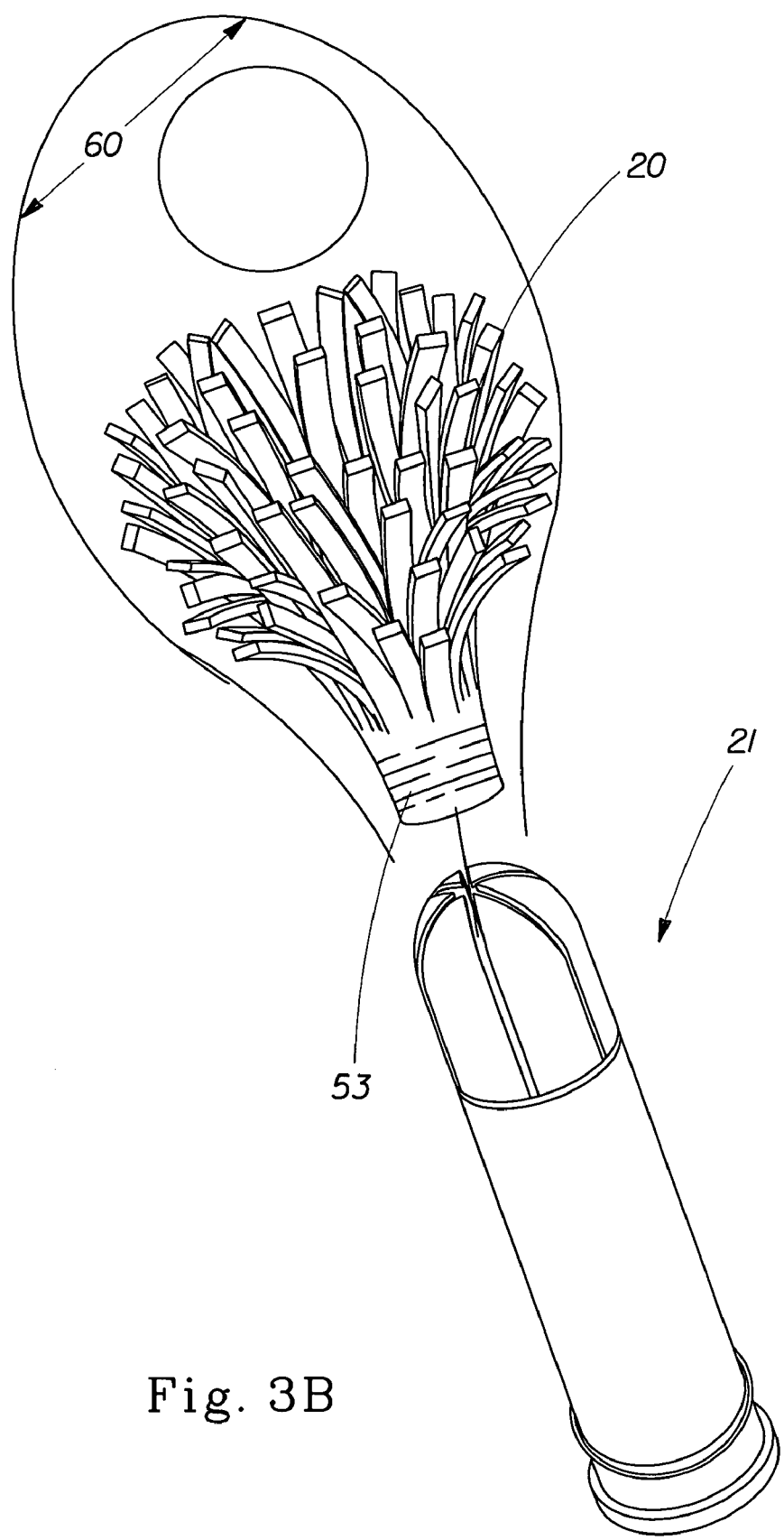
FIG. 3b is a perspective view of a tampon fitting within the vaginal cavity of a female user after the tampon has been expelled by the tampon applicator of the present invention.

By the term "side-to-side coverage," it is meant herein and as seen in FIG. 3b that the tampon 20 once directionally expelled, will have at least two sections thereof positioned outwardly toward the sides or walls of a female user's vaginal cavity.

By "side expulsion zone" is meant and as seen in FIG. 1a, a weakened region as compared to the side expulsion members 31. The side expulsion zone 35 is located between a first side expulsion member 31 and a second side expulsion member 31.

By "axial force," is meant and as seen in FIG. 1a, the force 40 applied along the longitudinal axis 45 in the direction of expelling the tampon 20 from the tampon applicator 21.

Referring to FIG. 1a, the present invention relates to directionally expelling tampon 20 into the vaginal cavity of a female user from a tampon applicator 21. Before expulsion of the tampon 20 from the tampon applicator 21, the tampon applicator 21 has an initial dimension 54. The tampon applicator 21 herein comprises a tampon holder tube 22 having a hollow interior portion (not shown), an interior surface (not shown), an outer perimeter 42, an exterior surface 25, a longitudinal axis 45, a first end 26 dimensioned for insertion into the body cavity (specifically the vaginal cavity of a female user), a second end 27 positioned oppositely to the first end 26, and a gripping portion 33.

Figure 6A:
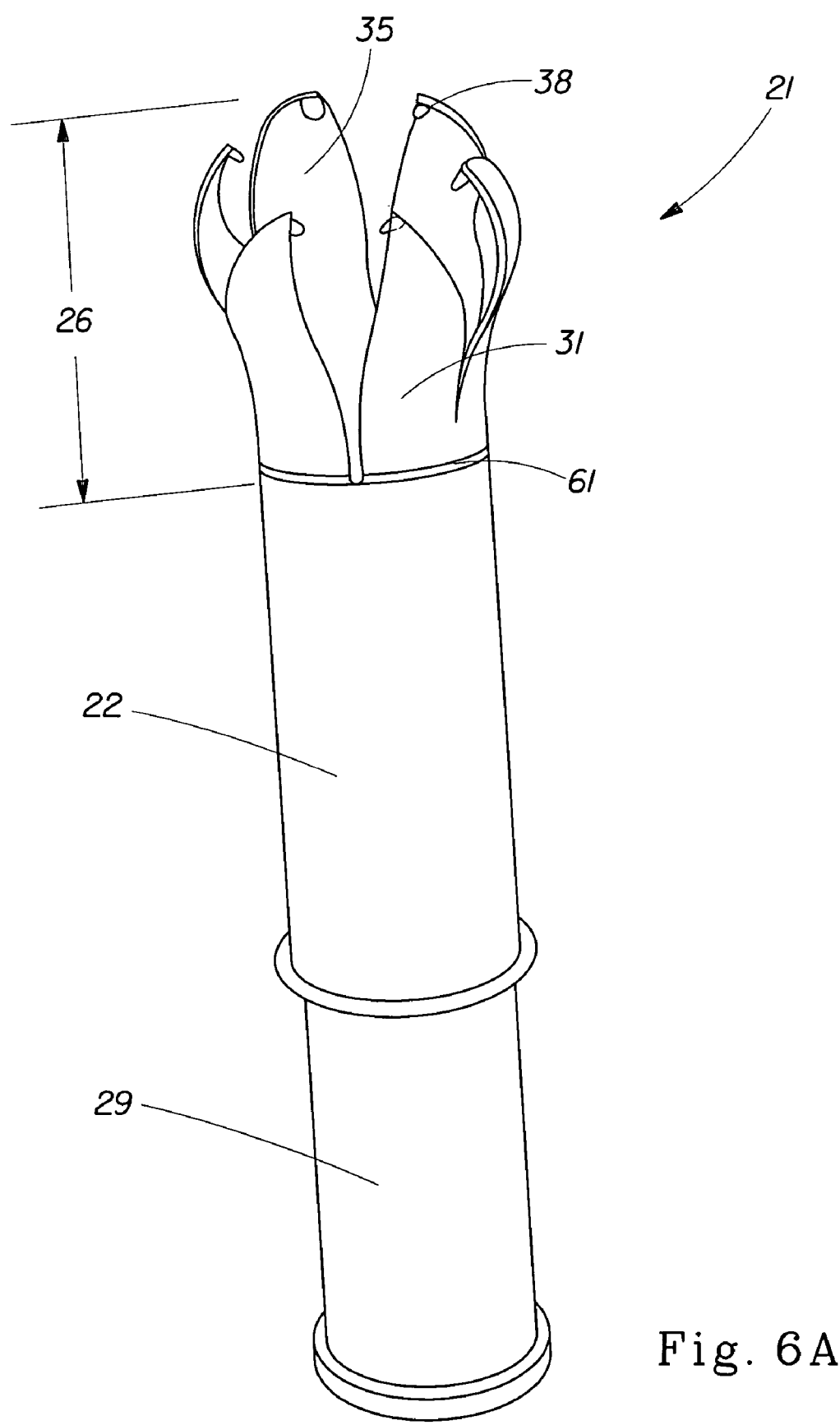
FIG. 6a is a perspective view of an alternative embodiment of a tampon applicator.

The first end 26 of the tampon holder tube 22 further comprises force controllers 30. The force controllers 30 are positioned adjacent to the side expulsion members 31. The weakened regions 61 are located around, at, or near, the base of the side expulsion members 31. The weakened regions 61 can extend circumferentially around, at, or near, the base of the side expulsion members 31. The force controllers 30 are separated by force controller sections 34 which may be between each force controller 30. The force controllers 30 and the force controller sections 34 are positioned at the top 44 of the first end 26. The end of the force controllers 30 may have projections 38 (FIG. 6a).

As noted above, the first end 26 comprises side expulsion members 31 which may be separated by side expulsion zones 35. The side expulsion members 31 and the side expulsion zones 35 are positioned along the outer perimeter 42 of the tampon holder tube 22. The combination of the force controllers 30, the force controller sections 34, the side expulsion members 31, and the side expulsion zones 35 is configured to laterally expand the tampon 20 during expulsion of the tampon 20 from the tampon applicator 21.

Alternatively, the tampon applicator 21 may include a plunger 29 that is slidably mounted in the tampon holder tube 22 distal to the first end 26. The plunger 29 is adapted to expel the tampon 20 from the tampon holder tube 22 with an axial force 40. However, such user activated expulsion may occur either by a plunger 29, plunger-like device, or digitally with a user's finger(s).

To use the tampon applicator 21 of the present invention the user will typically hold the tampon holder tube 22 in one hand at the gripping portion 33 on the same. When the plunger 29 is present, the user holds the end of the plunger 29, such as with her thumb and middle finger, and pushes the plunger 29 inwardly to slide the plunger 29 within the tampon holder tube 22. In practice, a user pushes the inserted plunger 29 until the entire tampon 20 is deployed from the tampon applicator 21. The user then pulls the entire tampon applicator 21 (i.e., with the plunger 29 inside) out of the user's vaginal opening.

The tampon applicator 21 has a pre-expelled state (FIG. 1a), a partially expelled state (FIG. 2), and an expelled state (FIG. 3a). During the pre-expelled state, as is readily seen in FIG. 1a, the tampon 20 sits within the tampon holder tube 22 and can remain snugly therein without any outside force to sustain its position in the tampon holder tube 22. As shown in FIG. 1a, during the tampon's pre-expelled state, the force controllers 30 have the initial dimension 54. FIG. 1b shows a top view of the tampon applicator 21 with the initial dimension of 54 and an outer perimeter 42. The force controllers 30 are separated by force controller sections 34. In addition, the force controller 30 may have a central opening 37.

Figure 2:
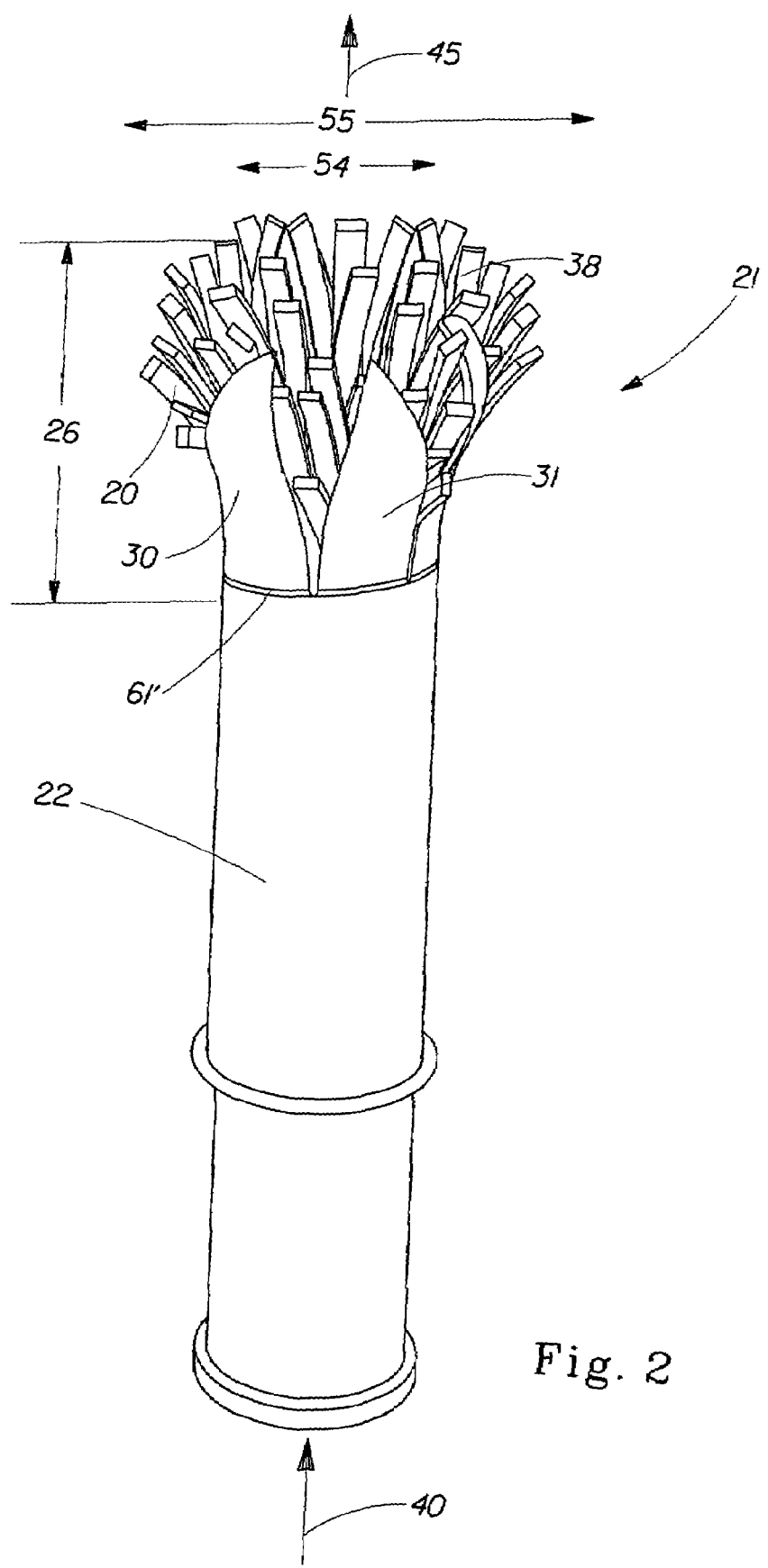
FIG. 2 is a perspective view of a tampon applicator and the tampon in its partially-expelled state.

In the partially expelled state, as is readily seen in FIG. 2, the tampon 20 is shown being directionally expelled with an axial force 40. When the axial force 40 is applied, the tampon 20 is pushed toward the first end 26. During this time, the tampon 20 can be held within the tampon applicator 21 by the force controllers 30. In one embodiment, the tampon 20 is spread by force controllers 30. Specifically, when the axial force 40 is applied, the axial force 40 is transferred to horizontal spreading force of the tampon 20 and the consequent separation of the engaged tampon 20. The force controllers 30 may contain projections 38. The force controllers 30 require a greater axial force 40 than the side expulsion members 31 to expel the tampon 20. FIG. 2 illustrates a tampon 20 partially positioned within and partially positioned without the tampon holder tube 22 of the tampon applicator 21 during the act of expulsion of the tampon 20. During expulsion, at least one side expulsion member 31 is expanded.

The combination of the weakened regions 61, force controllers 30, and the side expulsion members 31 aid the force controllers 30 to change from its first position with an initial dimension 54 in its pre-expelled state to its second position (FIG. 2) with side expulsion members 31 deployed width 55 in its partially expelled state and finally to a third position in its fully expelled tampon applicator 21 state (FIG. 3a).

FIG. 3a shows the tampon applicator 21 in its expelled state where the tampon 20 is expelled from the tampon applicator 21 along the longitudinal axis 45. The tampon applicator 21 has a tampon holder tube 22. The tampon holder tube 22 has a first end 26 dimensioned for insertion and a second end 27 opposite the first end 26. The first end 26 comprises the force controllers 30, side expulsion members 31, and side expulsion zones 35. The force controllers 30 may include projections 38 (FIG. 6a). In its expelled state, the tampon 20 is positioned into the vaginal cavity of a female user so that improved side-to-side coverage of the vaginal opening is achieved. After the tampon 20 is inserted vertically into the vaginal introitus, the tampon 20 may change its orientation to a position which is non-parallel to the tampon's 20 pre-expelled vertical position. As a result, the tampon's 20 position during insertion could be in a different orientation from the tampon's 20 position after insertion into the vaginal cavity. Contact of a female user's vaginal walls is a highly desired characteristic of a tampon 20 when it is worn during a female's menstruation period. Menses, whether highly viscous or less viscous, when flowing out of the user, follows the geometry of a female user's vaginal walls. In other words, menses may substantially flow along the vaginal walls of a female user. Regardless of the orientation of the tampon 20 within the vaginal cavity 60, FIG. 3b shows how such side-to-side coverage in the vaginal cavity 60 of the tampon 20 and placement of the trailing edge 53 of the tampon 20 within the vaginal cavity 60 is expected to occur when using the present tampon applicator 21.

Referring to FIG. 4, the tampon 20 can be inserted into the tampon applicator 21 in any orientation and/or folded in any manner (i.e., concave or convex). Despite the orientation of the tampon 20 upon insertion into the tampon applicator 21, the tampon 20 will still provide effective side-to-side coverage in the vaginal cavity. In one non-limiting example, the first portion 49 of the tampon 20 is inserted first into the second end 27 of the tampon holder 22 so that the first portion 49 of the tampon 20 expels first. In yet another non-limiting example, the second portion 50 of the tampon 20 is inserted first into the second end 27 of the tampon holder 22 so that the second portion 50 of the tampon 20 expels first. Referring to FIG. 5, the tampon 20 has a first portion 49 and a second portion 50. The second portion 50 of the tampon has a trailing edge 53. A withdrawal string 39 may also be attached.

FIG. 6a shows an alternative embodiment of a tampon applicator 21 comprising the tampon holder tube 22 and the plunger 29. The tampon holder tube 22 has a first end 26. The first end 26 comprises the side expulsion members 31 and side expulsion zones 35. To reduce the expulsion force required to bend the side expulsion members 31 open, a weakened region 61 is formed into the outer surface of tampon holder 22 around, at, or near, the base of the side expulsion members 31. The weakened regions 61 can extend circumferentially around, at, or near, the base of the side expulsion members 31. In use, as plunger 29 is pressed inwardly, side expulsion members 31 hinge at the weakened regions 61, and the tampon is expelled through the first end 26 of the tampon holder tube 22. The more the weakened regions 61 allow the side expulsion members 31 to hinge, the greater the horizontal spreading of the tampon. In this embodiment, the projections 38 are in the form of knobs.

Figure 6B:
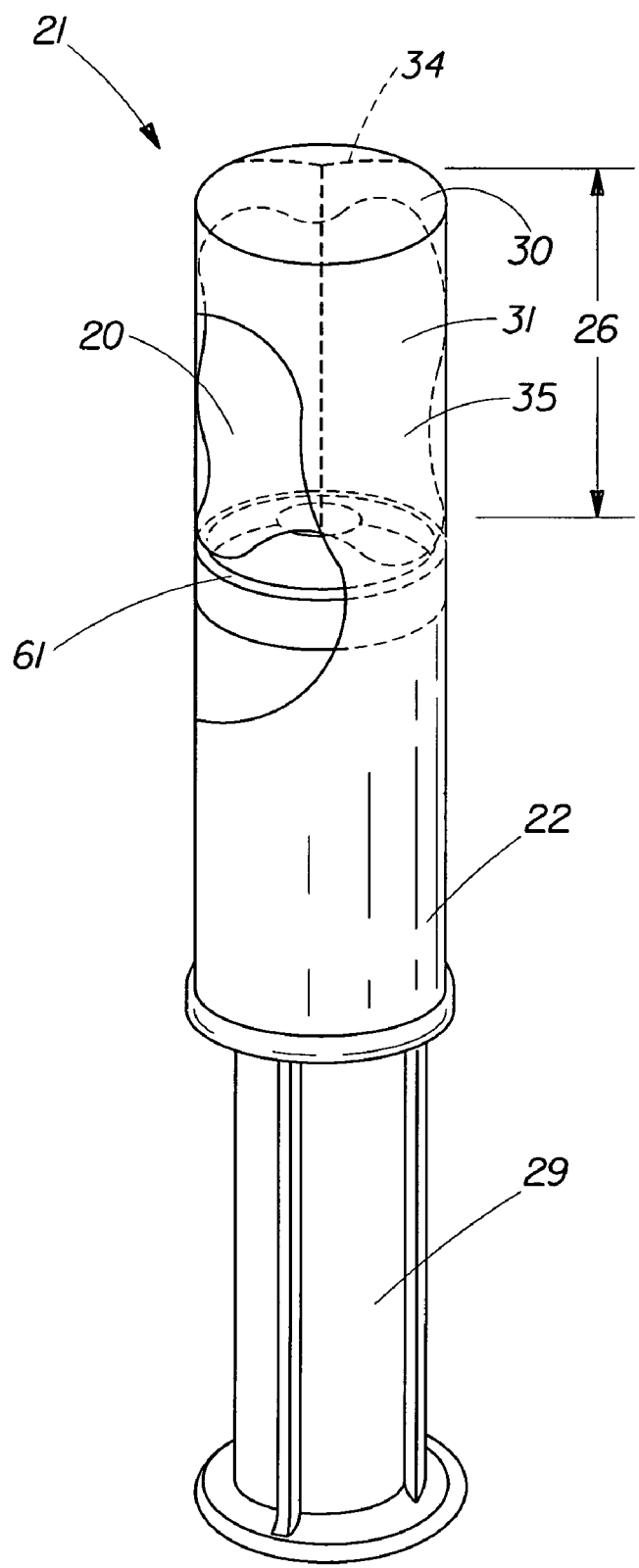
FIG. 6b is a perspective view of an alternative embodiment of a tampon applicator with the tampon.
Figure 7:
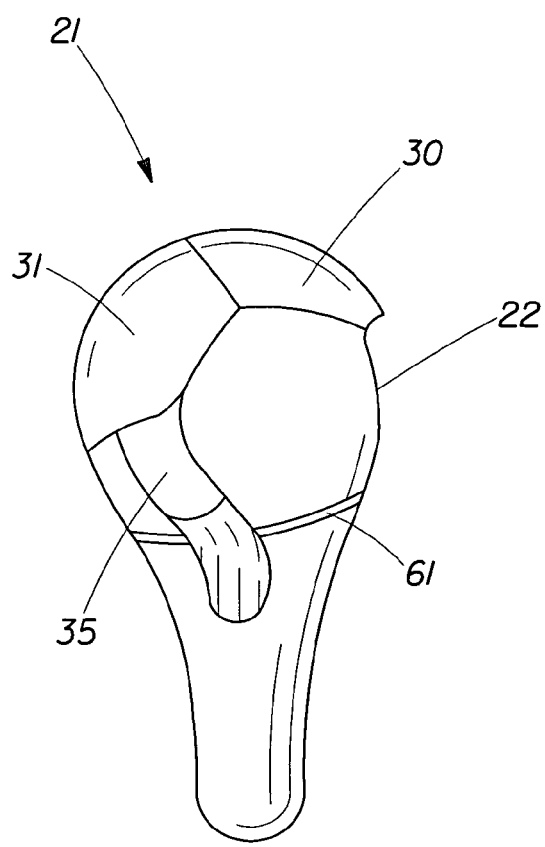
FIG. 7 is a perspective view of an alternative embodiment of a tampon applicator.
Figure 8:
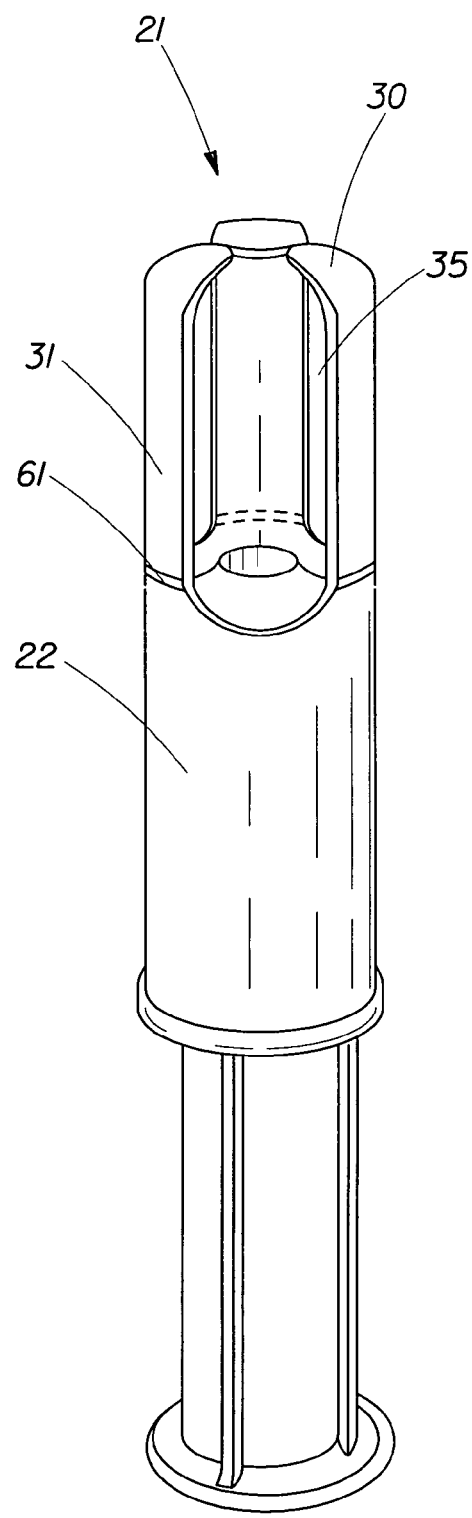
FIG. 8 is a perspective view of an alternative embodiment of a tampon applicator.
Figure 9:
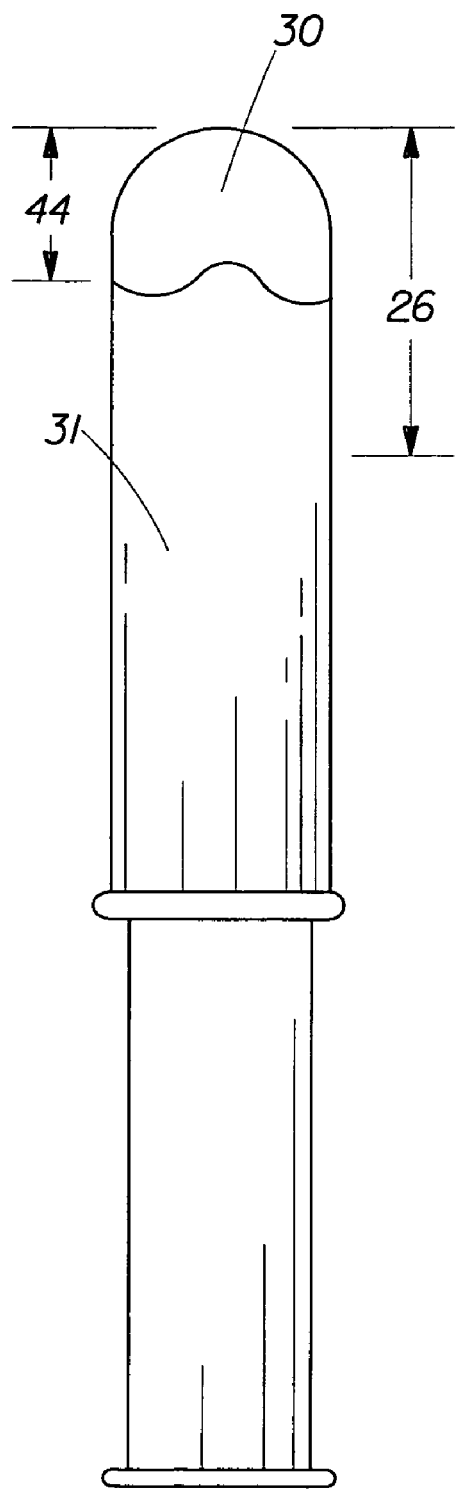
FIG. 9 is a perspective view of an alternative embodiment of a tampon applicator.
Figure 10:
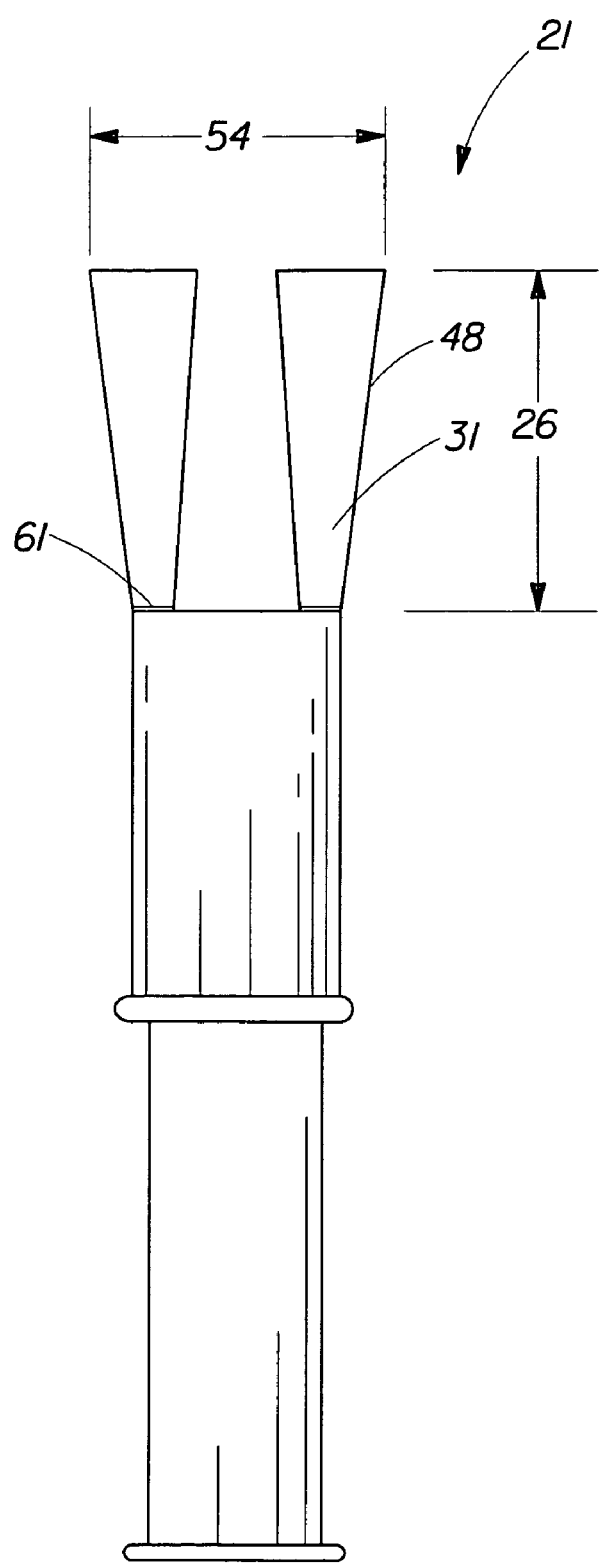
FIG. 10 is a perspective view of an alternative embodiment of a tampon applicator.
Figure 11:
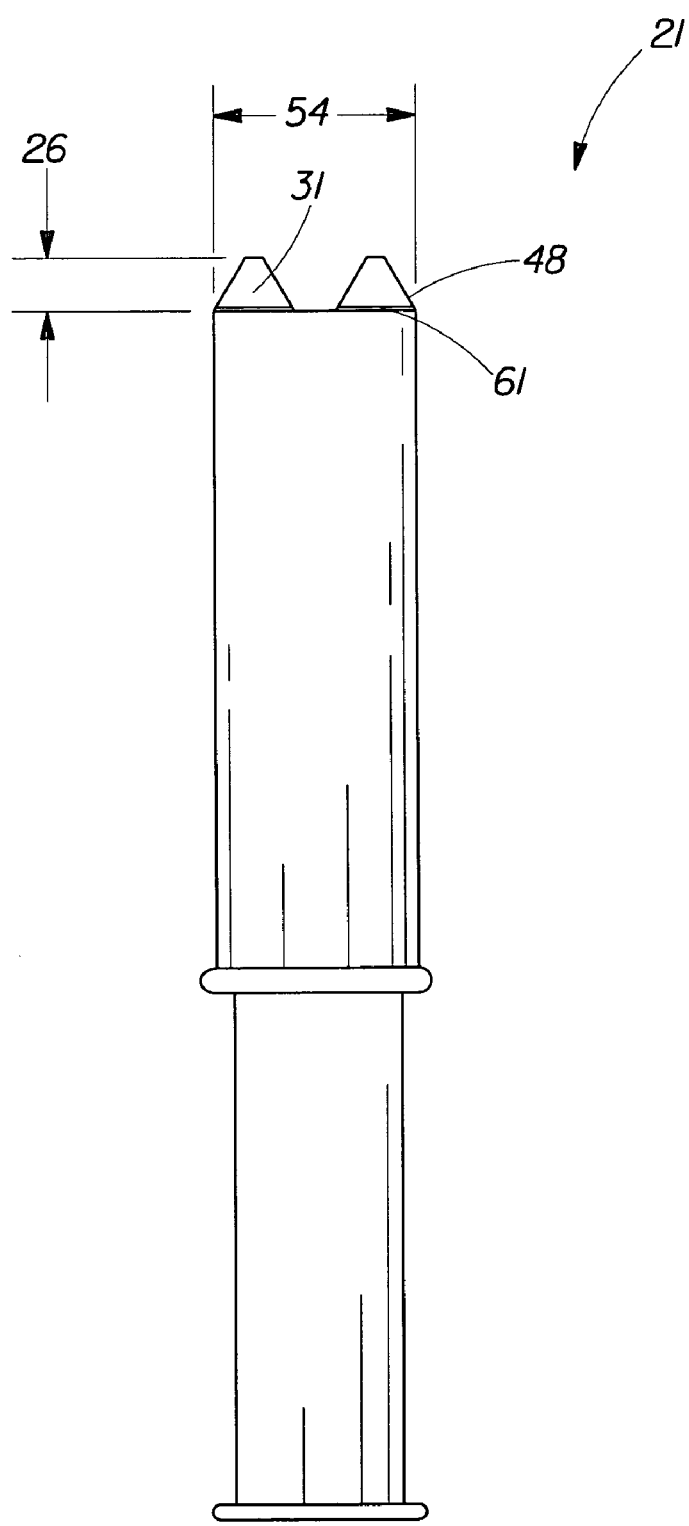
FIG. 11 is a perspective view of an alternative embodiment of a tampon applicator.
Figure 12:
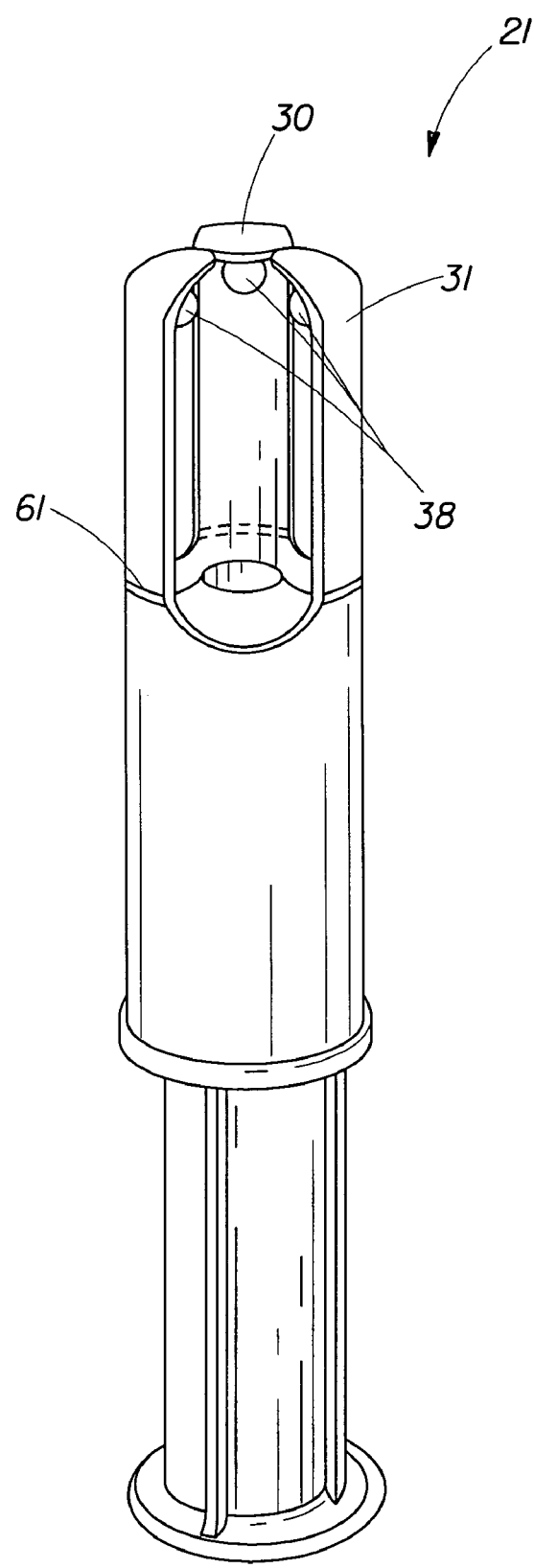
FIG. 12 is a perspective view of an alternative embodiment of a tampon applicator.

FIG. 6b shows yet another alternative embodiment of a tampon applicator 21 containing tampon 20 with a plunger 29. The tampon holder tube 22 has a first end 26. The first end 26 comprises the force controllers 30, force controller sections 34, side expulsion members 31, and side expulsion zones 35. Weakened regions 61 are formed into the outer surface of tampon holder 22 around, at, or near, the base of the side expulsion members 31. The weakened regions 61 can extend circumferentially around, at, or near, the base of the side expulsion members 31. The force controller sections 34 can comprise weakened regions. FIG. 7 and FIG. 8 show perspective views of alternative embodiments of tampon applicators 21 having force controllers 30 and side expulsion zones 35 which can be void. Weakened regions 61 are formed into the outer surface of tampon holder 22 around, at, or near, the base of the side expulsion members 31. The weakened regions 61 can extend circumferentially around, at, or near, the base of the side expulsion members 31. Alternatively, FIG. 9 shows another perspective view of an alternative embodiment of the side expulsion members 31 which can be one continuous film or sheet and the force controllers 30 which can be one continuous film or sheet. The force controllers 30 which are located at the top 44 of the first end 26 and the sides of the side expulsion members 31 may be completely enclosed. Moreover, FIG. 10 and FIG. 11 show another perspective embodiment of a tampon applicator 21 having an initial dimension 54. The sides 48 of the side expulsion members 31 which are located at the first end 26 may be non-uniform. Weakened regions 61 are formed into the outer surface of tampon holder 22 around, at, or near, the base of the side expulsion members 31. The weakened regions 61 can extend circumferentially around, at, or near, the base of the side expulsion members 31. FIG. 12 shows another perspective embodiment of a tampon applicator 21 having projections 38 located on the end of the force controller 30. Weakened regions 61 are formed into the outer surface of tampon holder 22 around, at, or near, the base of the side expulsion members 31. The weakened regions 61 can extend circumferentially around, at, or near, the base of the side expulsion members 31.

Below will detail each component of the tampon applicator 21.

I. Force Controller and Force Controller Section

Referring primarily to FIG. 1a, the force controllers 30 are positioned at the top 44 of the first end 26. As shown in FIG. 1b, each force controller 30 is separated from the other by respective sections 34. As shown in FIG. 1a, the force controllers 30 counter the axial force 40 which is applied along the longitudinal axis 45 when expelling the tampon 20 from the tampon applicator 21. Thus, the axial force 40 needed to expel the tampon 20 along the longitudinal axis 45 requires a greater force to expel the tampon 20 through the force controllers 30 than to expel the tampon 20 through the side expulsion members 31.

The force controllers 30 have a pre-expelled position (FIG. 1a), a partially expelled position (FIG. 2), and an expelled position (FIG. 3a).

FIG. 2 shows the position of the force controllers 30 when the tampon 20 is partially expelled. When a tampon 20 is being expelled by an axial force 40 applied along the longitudinal axis 45, the force controllers 30 expand beyond its initial dimension 54 along at least one of the side expulsion members 31. The force controllers 30 provide resistance to expelling the tampon 20 at the first end 26 thereof. In the present invention, the tampon 20 is deformable which allows the force controllers 30 to reshape the tampon 20. In other words, the tampon 20 for the lateral dimension change during expulsion.

The manufacturer of the tampon applicator 21 may vary the width of each force controller 30, the number of force controllers 30, the distance between each force controller 30, and the configuration of the force controllers 30.

The width of each force controller 30 can vary greatly. As seen in FIG. 1a, the width of each force controller 30 is a function of the length of the outer perimeter 42 of the tampon holder tube 22 and the width of the force controller sections 34 which are located between each force controller 30.

Any number of force controllers 30 may be utilized. Either an even or an odd number of force controllers 30 can be present. As shown in FIG. 1a and FIG. 1b, although six force controllers 30 are shown, additional force controllers 30 may give more positive engagement of the tampon 20.

Referring to FIG. 1a, the distance between each force controller 30 which extends along the outer perimeter 42 of the tampon holder tube 22 depends on the length of the outer perimeter 42 of the tampon holder tube 22, the width of each force controller 30, and the width of the force controller sections 34 which are located between each force controller 30. Moreover, the force controllers 30 can be equally spaced apart or they can be non-uniformly arranged. Uniformly arranged force controllers 30 are preferred, but randomly arranged force controllers 30 will work. For ease of manufacturing, it is preferred that the force controllers 30 be equally spaced relative to one another. The force controllers 30, however, may be unequally spaced relative to one another.

Referring to FIG. 1a, it is further noted herein that the shape or configuration of each of the force controllers 30 may vary as long as the force controllers 30 provides enough resistance when applying an axial force 40 in the longitudinal direction 45 to allow a substantial portion of the tampon 20 to be generally released at one time. One of skill in the art will readily recognize obvious variants on those presented in the patent application herein. One versed in the art can imagine that the shape of the force controllers 30 might be circular, square, rectangular, triangular, arced, curved, or any other conceivable shape possible as long as any such shape would work effectively to fully and properly provide resistance of the tampon 20 upon expulsion from the tampon holder tube 22, expel the tampon 20 from the tampon holder tube 22, and provide a greater axial force 40 to expel the tampon 20 along the longitudinal axis 45 from the force controllers 30 than from the side expulsion members 31. The force controller 30 is in no way limited by the size or shape that they may assume except that they should not substantially hinder directional expulsion of a tampon 20. As shown in FIG. 6b, in an alternative embodiment, the side expulsion members 31 may be covered with a thin film material which is not as strong as the force controllers' 30 material. The side expulsion members 31 could be hinged; scored; and/or a thin film. As also shown in FIG. 6b, the material of the force controllers 30 can be a polyethylene film and the side expulsion zones 35 can comprise of weakened regions as compared to the side expulsion members 31 which are perforated such that the force controllers 30 provide resistance to the tampon 20 while the plunger 29 forces the tampon 20 out of the force controllers 30.

Referring to FIG. 1b, the force controller sections 34 which separate each force controller 30 can be void areas, weakened regions, and/or regions covered in material. If the force controller sections 34 are covered in material, the material of the force controller sections 34 are not as strong as the force controllers' 30 material.

In one non-limiting example, the outer perimeter 42 can be about 60.96 mm. In this example, there can be three force controllers 30. Additionally, each force controller 30 can be about 6.35 mm and the force controller sections 34 between each force controller 30 can be about 13.97 mm.

In yet another non-limiting example, the outer perimeter 42 can be about 75 mm. In this example, there can be five force controllers 30. Additionally, each force controller 30 can be about 6.35 mm and the force controller sections 34 between each force controller 30 can be about 8.65 mm.

In one further non-limiting example, the outer perimeter 42 can be about 53.5 mm. In this example, there can be six force controllers 30. Additionally, each force controller 30 can be about 8 mm and the force controller sections 34 between each force controller 30 can be about 1 mm.

As shown in FIG. 2, each force controller 30 may comprise projections 38. The projections 38 may extend far enough into the center of the first end 26 to engage a tampon 20 disposed therein. The projections 38 may be any shape or size so long as the projections 38 provide resistance to expelling the tampon 20 by increasing the difficulty of expelling the tampon 20 out of the first end 26 thereof. The projections may take the form of a variety of shapes such as a rib, a notch, a knob, a hook, a perforation, an adhesive, VELCRO®, a bump, a ridge, or any mixtures thereof. As shown in FIG. 12, the projections 38 may be integrally formed on the end of each force controller 30. Alternatively, the projections 38 may be separately attached to the force controller 30.

As shown in FIG. 6a, any number of projections 38 may be utilized. Either an even or an odd number of projections 38 can be present. The number of projections 38 may vary as desired. Additional projections 38 may give more positive engagement of the tampon 20.

The projections 38 may be located anywhere on the force controllers 30. As shown in FIG. 6a, the projections 38 may be located at the end of the force controller 30. Furthermore, each force controller 30 does not have to have a projection 38.

Referring to FIG. 1a, as axial force 40 is applied along the longitudinal axis 45, the projections 38 (FIG. 6a) retain the tampon 20 while forcing the force controllers 30 to expand beyond its initial dimension 54 in its pre-expelled state. The projections 38 (FIG. 6a) allow the tampon 20 to laterally expand into the vagina and provide better vaginal coverage. Projections 38 (FIG. 6a) located at the end of the force controller 30 especially complement deformable tampons 20 which require less pressure to expand upon expulsion from the tampon holder tube 22.

As shown in FIG. 1b, the top view of the tampon holder tube 22 (FIG. 1a) forms a substantially rounded tip. The tampon holder tube 22 may have a central opening 37 at the top 44 (FIG. 1a) of the first end 26 (FIG. 1a). As shown in FIG. 1a, the rounded shape is useful to facilitate insertion of the tampon applicator 21 into the vaginal cavity. As shown in FIG. 7, in an alternative embodiment, the force controllers 30 form a substantially closed end configuration.

While not wishing to be bound by any particular theory, the force controllers 30 may be made from any polymeric material such as polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, and the like. The force controller 30 may also be made of paper, paperboard, cardboard, or any combinations thereof. Each force controller 30 may be composed of different materials or may be composed of substantially the same type of material. The force controller 30 need not be of the same material as the body of the tampon applicator 21.

The maximum width in which the tampon 20 is spread before leaving the tampon applicator 21 of the present invention is from about 20 mms to about 60 mms, depending on the tampon design.

II. Side Expulsion Member and Side Expulsion Zone

Referring primarily to FIG. 1a, the side expulsion members 31 aid in the trajectory of the tampon 20 because the side expulsion members' 31 axial force 40 to expel the tampon 20 is less than the axial force 40 to expel the tampon 20 from the force controllers 30. Because the side expulsion members' 35 axial force 40 is less, this aids in tampon's 20 proper placement which provides side-to-side coverage in the vaginal cavity. The axial force 40 is less because of the lack of resistance of the tampon 20 to move between the side expulsion members 31 as compared to the force controllers 30. In fact, when the tampon 20 is being expelled from the tampon holder tube 22, the force controllers 30 provide resistance while the side expulsion members' 31 reach a deployed width 55 (FIG. 2).

To reduce the expulsion force required to bend the side expulsion members 31 open, a weakened region 61 is formed into the outer and/or inner surface of tampon holder 22 around, at, or near, the base of the side expulsion members 31. The weakened regions 61 can extend circumferentially around, at, or near, the base of the side expulsion members 31. In use, as plunger 29 is pressed inwardly, side expulsion members 31 hinge at the weakened regions 61, and the tampon is expelled through the first end 26 of the tampon holder tube 22. The more the weakened regions 61 allow the side expulsion members 31 to hinge, the greater the horizontal spreading of tampon 20.

The weakened regions 61 may take a variety of forms such as differential wall thickness, grooves, perforations, slots, T-cuts, V-cuts, hinges, and mixtures thereof.

The weakened regions 61 can be any size or shape. Weakened regions 61 can be any size or shape as long as the weakened region 61 is able to reduce the force required to bend the side expulsion member 31. The weakened region 61 can be circular, square, rectangular, triangular, arced, curved, or any other conceivable shape possible. While the weakened regions 61 can be a wide range of shapes, it is preferred to use a member selected from the group consisting of straight grooves, tapered grooves, rectangular, flower petals, ellipses, and mixtures thereof.

The weakened regions 61 may be formed to have essentially identical sizes and shapes. In one non-limiting example, the tampon holder tube comprises ten weakened regions 61. In this example, each weakened region 61 can be identical to the other weakened regions 61. Alternatively, the weakened regions 61 may be formed to have various sizes and shapes as compared to another weakened region 61 on the tampon holder tube. In one non-limiting example, the tampon holder tube 22 has five weakened regions 61. However, each weakened region 61 may have a different geometric shape. Additionally, each weakened region 61 may have a different size.

The number of weakened regions 61 and the distance over which the weakened regions 61 extend may vary. Typically, the weakened regions 61 are formed at the base of the side expulsion members 31. The number of side expulsion members 31 may range from about 1 to infinity. Either an even or an odd number weakened regions 61 can be present. For ease of manufacturing, it is preferred that the weakened regions 61 be equally spaced relative to one another. The weakened regions 61, however, may be unequally spaced relative to one another.

The distance between each weakened region 61 depends upon the area of the side expulsion members 31 and the size and number of weakened regions 61.

More than one weakened region 61 can be formed at the base of the side expulsion members 31. If more than one weakened region 61 is formed, the weakened regions 61 may be arranged randomly or in a pattern. For example, weakened regions 61 can be arranged to form any three-dimensional geometric pattern known including, but not limited to, diagonal lines, straight lines, checkerboard, flowers, ovals, circles, rectangles, trapezoids, triangles, cones, alphabet letters, and mixtures thereof. Alternatively, the weakened regions 61 may be along the full length of the base of the side expulsion member 31 or may have thinned regions spaced intermittently along the length of the base of the side expulsion member 31. Alternatively, weakened regions 61 may be randomly arranged so that the multiplicity of weakened regions 61 may comprise merely a surface roughness in no apparent pattern. In addition, weakened regions 61 may be arranged such that the areas between the weakened regions 61 may form any geometric pattern known including, but not limited to, flowers, ovals, circles, rectangles, trapezoids, triangles, cones, alphabet letters, and mixtures thereof.

The side expulsion members 31 are positioned around the outer perimeter 42 of the tampon holder tube 22. The side expulsion members are below and adjacent to the force controllers 30. The side expulsion members 31 are separated from each other by respective side expulsion zones 35.

The side expulsion members 31 have a pre-expelled position with a side expulsion zone initial dimension 54 which is less than or equal to the outer perimeter 42 of the tampon holder tube 22. Furthermore, the side expulsion members 31 also have a side expulsion zone deployed width 55, shown in FIG. 2, which is greater than the outer perimeter 42 (FIG. 1) of the tampon holder tube 22 and the side expulsion zone's initial dimension 54. In other words, the side expulsion members 31 expand from a first transverse width 54 to a second transverse width 55. The second transverse width 55 is greater than the first transverse width 54. In one non-limiting example, the side expulsion members 31 may have a side expulsion zone initial dimension 54 of about ⅝ inch (about 1.6 cm) and a side expulsion zone deployed width 55 of about ¾ inch (about 1.9 cm) to about 1¼ inch (about 3.2 cm).

FIG. 2 shows the side expulsion members 31 when the tampon 20 is partially expelled. FIG. 3a shows the side expulsion members 31 in its expelled position.

The manufacturer of the tampon applicator 21 may vary the configuration of each side expulsion member 31, the number of side expulsion members 31, the width of each side expulsion member 31, and the distance between each side expulsion member 31.

Referring to FIG. 1a, the configuration of the side expulsion members 31 is preferably created to decrease the weakness along a portion of outer perimeter 42 of the tampon applicator 21. It is further noted herein that the shape or configuration of the side expulsion members 31 may vary as long as a substantial portion of the tampon 20 is allowed to expel and not hinder directional expulsion of the tampon 20. One of skill in the art will readily recognize obvious variants on those presented in the patent application herein. One versed in the art can imagine that the side expulsion members 31 might be circular, square, rectangular, triangular, or any other conceivable shape possible as long as any such shape would work effectively to fully and properly aid in the expulsion of the tampon 20 from the tampon holder tube 22. As shown in FIG. 10 and FIG. 11, the sides 48 of the side expulsion members 31 may be non-uniform.

Referring to FIG. 1a, any number of side expulsion members 31 may be utilized. Either an even or an odd number of side expulsion members 31 can be present. As shown in FIG. 1a, six side expulsion members 31 are shown.

Referring to FIG. 1a, the width of each of the side expulsion member 31 can vary greatly. The width of each side expulsion member 31 is a function of the outer perimeter 42 of the tampon holder tube 22 and the width of the side expulsion zones 35.

Referring to FIG. 1a, the distance between each side expulsion member 31 which extends along the outer perimeter 42 of the tampon holder tube 22 depends upon the outer perimeter 42 of the tampon holder tube 22, the width of the each side expulsion member 31, and the width of the side expulsion zones 35. They can be equally spaced apart or they can be non-uniformly arranged. Uniformly arranged side expulsion members 31 are preferred, but randomly arranged side expulsion members 31 will work. For ease of manufacturing, it is preferred that the side expulsion members 31 be equally spaced relative to one another. The side expulsion members 31, however, may be unequally spaced relative to one another.

The side expulsion members 31 are separated by side expulsion zones 35. The side expulsion zones 35 can be void areas, weakened regions, perforated areas, and/or thin areas. As shown in FIG. 6b, the configuration of the side expulsion members 31 may be one continuous sheet with weakened regions as side expulsion zones 35. As shown in FIG. 1a, the side expulsion members 31 may be separated from one another by void side expulsion zones 35.

In one non-limiting example, the outer perimeter 42 of the tampon holder tube 22 can be about 60.96 mm. In this example, there can be three side expulsion members 31. Additionally, each side expulsion member 31 can be about 6.35 mm and the side expulsion zones 35 between each side expulsion member 31 can be about 13.97 mm.

In yet another non-limiting example, the outer perimeter 42 of the tampon holder tube 22 can be about 75 mm. In this example, there can be five side expulsion members 31. Additionally, each side expulsion member 31 can be about 6.35 mm and the side expulsion zones 35 between each side expulsion member 31 can be about 8.65 mm. In this example, the length of the side expulsion members 31 and the side expulsion zones 35 can be about 35.56 mm.

In one further non-limiting example, the outer perimeter 42 can be about 53.5 mm. In this example, there can be six side expulsion members 31. Additionally, each side expulsion members 31 can be about 8 mm and the side expulsion zones 35 between each side expulsion member 31 can be about 1 mm. In this example, the length of the side expulsion members 31 and the side expulsion zones 35 can be about 20 mm.

FIG. 6a shows an alternative embodiment of a tampon applicator 21 comprising the tampon holder tube 22 and the plunger 29. The tampon holder tube 22 has a first end 26. The first end 26 comprises the side expulsion members 31 and side expulsion zones 35. To reduce the expulsion force required to bend the side expulsion members 31 open, a weakened region 61 is formed into the outer surface of tampon holder 22 around, at, or near, the base of the side expulsion members 31. The weakened regions 61 can extend circumferentially around, at, or near, the base of the side expulsion members 31. In use, as plunger 29 is pressed inwardly, side expulsion members 31 hinge at the weakened regions 61, and the tampon is expelled through the first end 26 of the tampon holder tube 22. The more the weakened regions 61 allow the side expulsion members 31 to hinge, the greater the horizontal spreading of tampon 20. In this embodiment, the projections 38 are in the form of knobs.

In an alternative embodiment, as seen in FIG. 9, the side expulsion members 31 may have one continuous film or sheet and the force controllers 30 may have one continuous film or sheet. The sheet of the force controllers 30 may completely enclose the top 44 of the first end 26. The sheet or film of the side expulsion members 31 may completely enclose the sides. The sheet of the side expulsion members 31 and the sheet of the force controller 30 may overlap one another. The sheet for the side expulsion members 31 and the sheet for the force controllers 30 can be sealed to one another by any known means in the art such as heat seal, glue, or mold. This film or sheet protects the tampon 20 from contamination. The sheet or film for the side expulsion members 31 is not as strong as the film or sheet for the force controllers' 30 material.

The side expulsion members 31 may be composed of different materials or may be composed of substantially the same type of material.

III. Tampon

Referring to FIG. 1a, a tampon 20 may be stored within the tampon holder tube 22. As shown in FIG. 5, in one preferred embodiment herein, the tampon applicator 21 can comprise tampon 20, such as that disclosed in currently pending and commonly assigned, U.S. patent application Ser. No. 10/836,892, filed Apr. 30, 2004, entitled "Tampon Comprising a Plurality of Strips or Cords," to Minoguchi, et al, Case 9615.

IV. Tampon Applicator Materials

Different tampon applicator parts can be constructed from different materials and processes.

A. Tampon Holder Tube Materials

Referring primarily to FIG. 1a, the tampon holder tube 22 can be constructed from similar materials to other tampon holder tubes 22 known in the art of the type used in tampon applicators currently in use. Examples of other such tampon holder tubes are disclosed in U.S. Pat. No. 5,346,468 issued to Campion, et al. on Sep. 13, 1994 and U.S. Pat. No. 5,558,631 issued to Campion, et al. on Sep. 24, 1996. The tampon holder tube 22 can be of any suitable cross-sectional shape. Suitable cross-sectional shapes include, but are not limited to circular, oval, flattened circular, and elliptical. Preferably, the tampon holder tube 22 has a circular cross-sectional configuration.

The tampon holder tube 22 may be made from any polymeric material such as polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, and the like. The tampon holder tube 22 may also be made of paper, paperboard, cardboard, or any combinations thereof. Accordingly, the exterior surface 25 of the tampon applicator 21 may be constructed from any suitable smooth plastic material.

B. Plunger Materials

Referring primarily to FIG. 1a, the plunger 29 can be used to expel the tampon 20 from its position within the tampon holder tube 22 when the plunger 29 is pushed manually into the tampon holder tube 22. The plunger 29 is usually pulled out to its operative position when the tampon holder tube 22 is placed in the vaginal cavity. Plunger 29 is then telescoped back into the tampon holder tube 22 towards the second end 27 thereof, pushing the tampon 20 through the first end 26 spreading open the yieldable force controller 30 and side expulsion zone(s) 31.

The plunger 29 can be any type of component that is suitable for this purpose. The plunger 29 can be constructed similarly to plungers of the type used in tampon applicators currently in use. An example of a suitable plunger is disclosed in U.S. Pat. No. 5,346,468 issued to Campion, et al. on Sep. 13, 1994 and U.S. Pat. No. 5,558,631 issued to Campion, et al. on Sep. 24, 1996. Moreover, the plunger 29 may be made from any polymeric material such as polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, and the like. The plunger 29 may also be made of paper, paperboard, cardboard, or any combinations thereof. It should also be understood that the plunger 29 is an optional component for use with the tampon applicator 21 and that the tampon applicator 21 will be fully functional if the plunger 29 is omitted, i.e., a user must insert and push the tampon 20 through the tampon applicator 21 digitally.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon and a tampon applicator in combination for expulsion of said tampon into a vaginal cavity of a female user, comprising:

said tampon applicator comprising a tampon holder tube and a plunger;

said tampon holder tube comprising a hollow interior portion, an interior surface, an exterior surface, a longitudinal axis, an outer perimeter, a first end dimensioned for insertion into said vaginal cavity, a second end positioned oppositely to said first end, a force controller positioned at said first end of said tampon holder tube, at least one side expulsion member positioned at said first end of said tampon holder tube, wherein said side expulsion member comprises a weakened region, said weakened region is selected from the group consisting of a groove, perforation, slot, T-cut, V-cut, and hinge;

said tampon comprising an insertion end and a withdrawal end, a body comprising a first end, a center, and a second end; said body comprising a joined portion; said body comprising a plurality of absorbent strips joined at said joined portion;

wherein said strips being selected from the group consisting of sheets, tissues, webs, nonwoven materials, films, woven materials, absorbent foams, superabsorbent polymers, and mixtures thereof, said tampon being housed within said hollow interior portion of said tampon holder tube in a pre-expelled position; and said plunger being slidably mounted in said hollow interior portion of said tampon holder tube, said plunger being adapted to expel said tampon through said force controller.

2. The tampon and tampon applicator of claim 1 wherein said joined portion is at said first end.

3. The tampon and tampon applicator of claim 1 wherein said joined portion is at said second end.

4. The tampon and tampon applicator of claim 1 wherein said joined portion is at said center.

5. The tampon and tampon applicator of claim 1 wherein said tampon holder tube comprises a plurality of side expulsion members.

6. The tampon and tampon applicator of claim 1 wherein said side expulsion member comprises said weakened region located at said base of said side expulsion member.

7. The tampon and tampon applicator of claim 1 wherein said tampon holder tube further comprises a side expulsion zone.

8. The tampon and tampon applicator of claim 1 wherein said tampon when partially expelled from said tampon holder tube is wider than said tampon holder tube.

9. The tampon and tampon applicator of claim 7 wherein said side expulsion zone has a slot, arc, window, or curved configuration.

10. The tampon and tampon applicator of claim 7 wherein said side expulsion zone is a void.

11. The tampon and tampon applicator of claim 7 wherein said side expulsion zone is a weakened area.

12. The tampon and tampon applicator of claim 1 wherein said force controller further comprises a projection.

13. The tampon and tampon applicator of claim 12 wherein said projection is selected from a group consisting of a rib, notch, perforation, hook, knob, bump, ridge, adhesive, and Velcro.

14. The tampon and tampon applicator of claim 1 wherein said side expulsion member further comprises a projection.

15. A tampon and a tampon applicator in combination for expulsion of said tampon into a vaginal cavity of a female user, comprising:

said tampon applicator comprising a tampon holder tube;

said tampon holder tube comprising a hollow interior portion, an interior surface, an exterior surface, a longitudinal axis, an outer perimeter, a first end dimensioned for insertion into said vaginal cavity, and a second end positioned oppositely to said first end;

said tampon holder tube comprising a force controller and a side expulsion member each positioned at said first end of said tampon holder tube, wherein said side expulsion member comprises a weakened region, said weakened region is selected from the group consisting of a groove, perforation, slot, T-cut, V-cut and hinge;

said tampon being housed within said hollow interior portion of said tampon holder tube in a pre-expelled position; and said tampon comprising an insertion end and a withdrawal end, a body comprising a first end, a center, and a second end; said body comprising a joined portion; said body comprising a plurality of absorbent strips joined at said joined portion;

wherein said strips being selected from the group consisting of sheets, tissues, webs, nonwoven materials, films, woven materials, absorbent foams, superabsorbent polymers, and mixtures thereof.

16. A tampon and a tampon applicator in combination for expulsion of said tampon into a vaginal cavity of a female user, comprising:

said tampon applicator comprising a tampon holder tube;

said tampon holder tube comprising a hollow interior portion, an interior surface, an exterior surface, a longitudinal axis, an outer perimeter, a first end dimensioned for insertion into said vaginal cavity, and a second end positioned oppositely to said first end;

said tampon holder tube comprising a force controller and a side expulsion member each positioned at said first end of said tampon holder tube, wherein said side expulsion member comprises a weakened region, said weakened region is selected from the group consisting of a groove, perforation, slot, T-cut, V-cut, and hinge, said tampon being housed within said hollow interior portion of said tampon holder tube in a pre-expelled position;

said tampon comprising an insertion end and a withdrawal end, a body comprising a first end, a center, and a second end; said body comprising a joined portion; said body comprising a plurality of absorbent strips joined at said joined portion;

wherein said strips being selected from the group consisting of sheets, tissues, webs, nonwoven materials, films, woven materials, absorbent foams, superabsorbent polymers, and mixtures thereof, and wherein said force controller comprises a projection.

* * * * *